United States Patent
Vaez-Iravani

(10) Patent No.: US 6,578,961 B2
(45) Date of Patent: *Jun. 17, 2003

(54) MASSIVELY PARALLEL INSPECTION AND IMAGING SYSTEM

(75) Inventor: Mehdi Vaez-Iravani, Santa Clara, CA (US)

(73) Assignee: KLA-Tencor Corporation, San Jose, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/819,347

(22) Filed: Mar. 27, 2001

(65) Prior Publication Data

US 2001/0048521 A1 Dec. 6, 2001

Related U.S. Application Data

(63) Continuation of application No. 09/161,864, filed on Sep. 28, 1998, now Pat. No. 6,208,411.

(51) Int. Cl.[7] .............................................. G01N 21/88
(52) U.S. Cl. ................................................... 350/237.2
(58) Field of Search ........................... 356/237.2, 237.3, 356/237.4, 237.5, 609

(56) References Cited

U.S. PATENT DOCUMENTS

| | | | | |
|---|---|---|---|---|
| 4,629,324 A | * | 12/1986 | Stern | ........................... 356/609 |
| 5,737,084 A | * | 4/1998 | Ishihara | ...................... 356/609 |
| 6,043,932 A | * | 3/2000 | Kusunose | .................... 359/368 |
| 6,208,411 B1 | * | 3/2001 | Vaez-Iravani | ............ 356/237.2 |

* cited by examiner

Primary Examiner—Richard A. Rosenberger
(74) Attorney, Agent, or Firm—Smyrski & Livesay, LLP

(57) ABSTRACT

A massively parallel inspection and imaging system is provided which employs multiple focused beams to illuminate a specimen. Laser light energy passes through a relatively low resolution diffraction grating or digital optical element, which is either one or two dimensional, and concentrates the transmitted energy into multiple discrete directions or orders. The beams split by the diffraction grating pass through a beam expander or telescope and are recombined onto an optical element and diverted toward the specimen. On reflection toward the specimen, the beams diverge again toward a focusing objective. The resultant light thus comprises multiple focused beams, and a relatively large area of the specimen is illuminated simultaneously by these beams. Upon reflection of the light from the sample, light passes back through the focusing objective in multiple beams, and the beams converge toward the optical element and diverge outward in collimated beams. The collimated beams pass through a focusing lens, which brings all beams onto foci on a detector array. Scanning of patterned wafers by the system may occur using coordinated motion of both the scanning beam and the wafer. To achieve proper orientation and observation, the stage speed in the cross direction is set at the ratio of the distance between the first and last lines divided by the period of the scanner.

11 Claims, 4 Drawing Sheets

MASSIVELY PARALLEL INSPECTION AND IMAGING SYSTEM

This is a continuation of U.S. patent application Ser. No. 09/161,864, filed Sep. 28, 1998 now U.S. Pat. No. 6,208,411.

BACKGROUND OF THE INVENTION

1. Field of the Invention

The present invention relates generally to the art of optical inspection of specimens, such as semiconductor wafers, and more specifically to a massively parallel inspection system having relatively large fields of view.

2. Description of the Related Art

Optical inspection techniques for small specimens, such as features on semiconductor wafers, have previously utilized confocal microscopy to locate and examine the desired site. Confocal microscopy or confocal imaging each provide a variety of limitations, most particularly a relatively narrow field of view, or spot width, depending on the desired resolution of the image received and the overall quality of the components employed.

The essence of confocal microscopy or confocal imaging is to perform a double imaging of the specimen utilizing point illumination and a point detector. For example, the use of confocal imaging entails focusing a beam transmitted and reflected on the semiconductor wafer using an objective lens, wherein the area examined at any given time is on the order of 20–50 microns on each side. The problem with this narrow field of view is that inspection of a wafer having dimensions in excess of 100 square inches can be extremely time consuming.

Further, this single spot inspection system, wherein inspection comprises scanning using a single narrow spot, requires two dimensional scanning. In such an arrangement, the single spot passes over a linear portion of the sample while recording data, then moves one spot diameter or a fraction of a spot diameter over and passes over the next linear portion of the sample while recording data. The system thus iteratively progresses through inspection of the wafer using this stepping technique.

Different methodologies have been employed to improve the throughput of confocal microscopy and inspection systems, but these systems typically address improving scanning speed and accuracy using the smaller spot width mentioned above. The use of large spots removes much of the confocal advantage and is therefore undesirable.

Systems employing beam expanders have been utilized previously, but such systems have been directed toward alignment issues. Such a system is illustrated in U.S. Pat. No. 5,231,467 to Takeuchi et al. The Takeuchi system provides a compensating optical system which utilizes a diffraction grating on a semiconductor wafer to diffract the incoming light beam. However, this does not significantly alter the area on the specimen which can be observed in a given time period, but rather provides position alignment assistance when different wavelength light is used on the two samples to be aligned.

Further, systems employing multiple spot confocal imaging have also been available. U.S. Pat. No. 5,737,084 to Ishihara illustrates a system in which a multi-spot confocal arrangement is used to measure three-dimensional shapes. U.S. Pat. No. 5,248,876 to Kerstens et al. describes a similar system for imaging at different heights. In both these systems an array of pinholes is utilized both with and without an accompanying lens array in front of an extended source of light to generate a plurality of point sources. These point sources are then brought into focus on the sample by the action of an objective lens. The reflected beams are directed back through the same pinhole array, or another matching array of pinholes. One drawback of such an approach is that the illumination position and collection pinholes must be precisely matched over the entire array. This requires a very high degree of mechanical stability, and implies a relatively large sensitivity to unwanted vibrations. Even in a situation where the illumination and collection pinhole arrays are one and the same, as in the case of U.S. Pat. No. 5,737,084, the relative size of the pinholes with respect to the eventual pixel size in the detector array still requires precise alignment between the detector and pinhole arrays. A further problem with the identical illumination/pinhole array arrangement is the possibility of stray light that may find its way onto the unintended detector pixels. Special precautions are thus necessary to eliminate this risk. In addition, the patent only describes a system capable of generating a sampled version of the image of the object under examination. No provisions are made for the scanning of either the beams or the sample to cover the entire sample, and no methodology is taught to achieve the same. It is important to note that the scanning action in a multi-spot system should ideally be different from that practiced in the case of a single spot system so that proper advantage is taken of the multiplicity of the beams.

Yet another consideration that pertains to these references is the fact that they rely on a precise action of the microlens/pinhole structures to generate high quality beams for each individual focal spot. This precision may not be easily attainable, particularly for applications in very high resolution imaging, where the quality of the wavefront in each beam is paramount.

An important aspect of current scanning applications is the operation of such a system as a dark-field imaging/inspection system. This issue is addressed in U.S. Pat. No. 5,248,876, which teaches the use of polarization, and polarization rotating components, to separate scattered radiation from the spectrally reflected light. Such an approach has undesirable consequences in that it essentially transforms the system into a polarizing microscope and requires the use of polarized light of a given direction to image the specimen. This polarization method also requires the use of two orthogonal polarizers in an arrangement, with one being positioned annularly with respect to the other, which forms the central region of a circular aperture. In dark-field imaging/inspection, the ability to respond to all features regardless of the specificity of their orientation or polarization behavior is extremely important. The inability to provide this feature is a significant drawback.

The references cited above also only address usage of multiple normally, or nearly normally, incident beams with respect to the sample. They do not teach the methodology under which the multi-spot arrangement could be used in obliquely incident configurations, where great advantage is gained in detecting minute defects on the surface of specimens such as silicon wafers.

It is therefore an object of the current invention to provide a system for increasing the inspected area of a confocal microscopic system, thereby increasing throughput, while at the same time offering minimal optical or confocal degradation under both brightfield and darkfield scanning.

It is a further object of the current invention to provide a system for optical inspection which has improved throughput performance and does not require significant modifications to existing hardware or software.

It is still a further object of the current invention to provide a system for detecting defects on a semiconductor wafer, the system having the ability to detect defects in a relatively short time period.

It is yet another object of the current invention to provide an optical inspection system which is relatively impervious to mechanical vibrations and stray light, and does not require precise alignment between detector and collection array.

It is yet another object of the current invention to provide a darkfield imaging optical inspection system which does not require use of polarized light of a given direction in the imaging process, and responds to all features irrespective of the specificity of their orientation or polarization behavior.

SUMMARY OF THE INVENTION

According to the present invention, there is provided a massively parallel inspection and imaging system which employs a plurality of focused beams to illuminate the sample. Light energy is emitted from a laser and passes through a relatively low resolution diffraction grating or preferably a digital optical element (multi spot generator). The low resolution diffraction grating concentrates the transmitted energy into multiple discrete directions or orders. The low resolution diffraction grating can be either a linear or two dimensional grating. The beams split by the diffraction grating pass through a telescope and are recombined onto a beamsplitter/scanner and are diverted toward the specimen. On reflection downward, the beams diverge again toward a focusing objective, wherein the focal plane of the focusing objective coincides with the apparent plane of light splitting.

The resultant light thus consists of a number of focused beams, and the sample is illuminated by these beams simultaneously. Upon reflection of the light from the sample, the light passes back through the focusing objective in a number of beams, and the beams converge toward the beamsplitter. The beamsplitter reflects a portion of the energy in the collimated beams. The collimated beams pass through a focusing lens, which brings all beams onto foci on a detector array, which may be one or two dimensional discrete photodiodes, CCD, or any other reasonable detection array.

Scanning in the system may occur in various ways. The system may pass the sample iteratively by scanning it beneath the objective in a raster fashion in the x and y directions, or alternately by spinning the sample about a central axis. Using these types of scanning methods, the position of the focused spots on the CCD or sensor array elements is fixed. Alternately, the system may employ a mechanical raster scanning arrangement of the beams using a scanning arrangement such as a resonant mirror scanner. In this case, both the sample and the beams are mechanically rastered. In this situation, for example, the beams may repeatedly move backward and forward in the x direction while staying fixed in the y direction, while the sample makes smaller movement in the y direction and does not move in the x direction.

Another potential scanning technique for the current invention may be used during the inspection of a patterned wafer. Using motion of both the scanning beam and the wafer, movement of each must be coordinated to properly observe the Manhattan "streets", or tracks of wiring, located on the wafer. To achieve proper orientation and observation, the stage speed in the cross direction is set at the ratio of the distance between the first and last lines divided by the period of the scanner. When the wafer reaches the end of a swath, the scanning must occur in the opposite direction. The same strategy as described above may be employed, with the exception of a reversal of the fast scanning direction, or a re-orientation of the stage or scanner to provide the reverse angular disparity between the scanner and the wafer. This reverse scanning technique may be employed by using a bidirectional scanner such as a galvo mirror and taking data on the reverse path across the wafer. Alternately, the stage may perform a fast return to one swath width plus one pixel from the position where the prior scan began, and the next swath of data is then taken in the same manner as before.

Other objects, features, and advantages of the present invention will become more apparent from a consideration of the following detailed description and from the accompanying drawings.

DETAILED DESCRIPTION OF THE INVENTION

The inventive system herein is intended for use with a readily available wafer inspection platform with modifications to specific portions of such systems.

Figure 1:
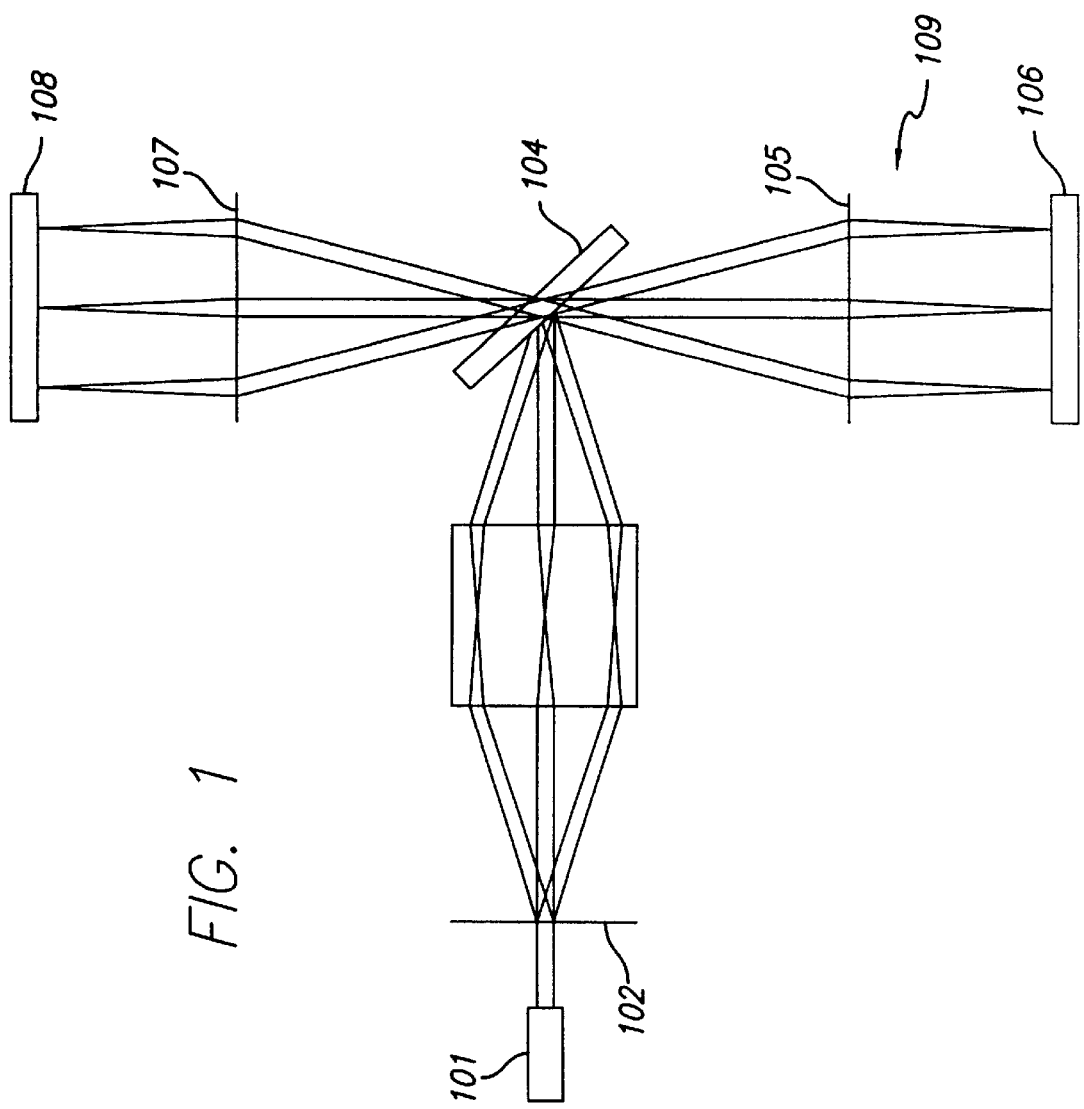
FIG. 1 illustrates a side view of the inventive massively parallel inspection and imaging system disclosed herein.

The present invention employs a plurality of focused beams to illuminate the sample, wherein the light emitted from laser 101 is passed through a relatively low resolution diffraction grating, or preferably a digital optical element (multispot generator). A simplified drawing of the concept employed herein is illustrated in FIG. 1. As shown in FIG. 1, laser 101 passes light through low resolution diffraction grating 102. Low resolution diffraction grating 102 is an array of fine, parallel, equally spaced grooves, or rulings, on a transparent substrate wherein such grooves produce diffractive and mutual interference effects which concentrate the transmitted energy in discrete directions or orders. The low resolution diffraction grating 102 can be either a linear or two dimensional grating which splits the light into a number of orders along a line, or in 2 dimensions depending on the type of grating employed. A digital optical element in this case is an array of repetitive structures which produce a plurality of diverging beams from an input beam. The advantage of digital optical elements is that they can be designed to produce essentially uniform power distribution among the beams, with little wastage.

The beams pass through a telescope 103. At the output of the telescope 103, the beams are recombined onto the beamsplitter 104 and are thereby reflected downward toward the specimen 106. It should be noted that as shown in FIG. 1, the multiple beams converge when emitted from telescope 103 toward beamsplitter 104. On reflection from the beamsplitter 104 downward toward the specimen 106, the beams diverge again toward the focusing objective 105. The focal plane of the focusing objective 105 coincides with the apparent plane of splitting of the light.

The resultant light thus consists of a number of focused beams 109, and the sample is illuminated by these beams simultaneously. Upon reflection of the light from the sample or specimen 106, the light passes back through the focusing objective 105 in a number of focused beams, and the focused beams converge toward beamsplitter 104. Beamsplitter 104 performs a beamsplitting function on the light at this point, transmitting a portion of the light as shown in the form of collimated beams. These collimated beams pass through focusing lens 107, where the focusing lens 107 brings all beams onto foci on a detector array 108. Detector array 108 may be a one dimensional or two dimensional array of discrete photo detectors, CCD (Charged-Coupled Device), or any other reasonable detection array. Since each element of a CCD acts as a confined area independent detector, each point in the array produces an independent confocal imaging signal.

Figure 2:
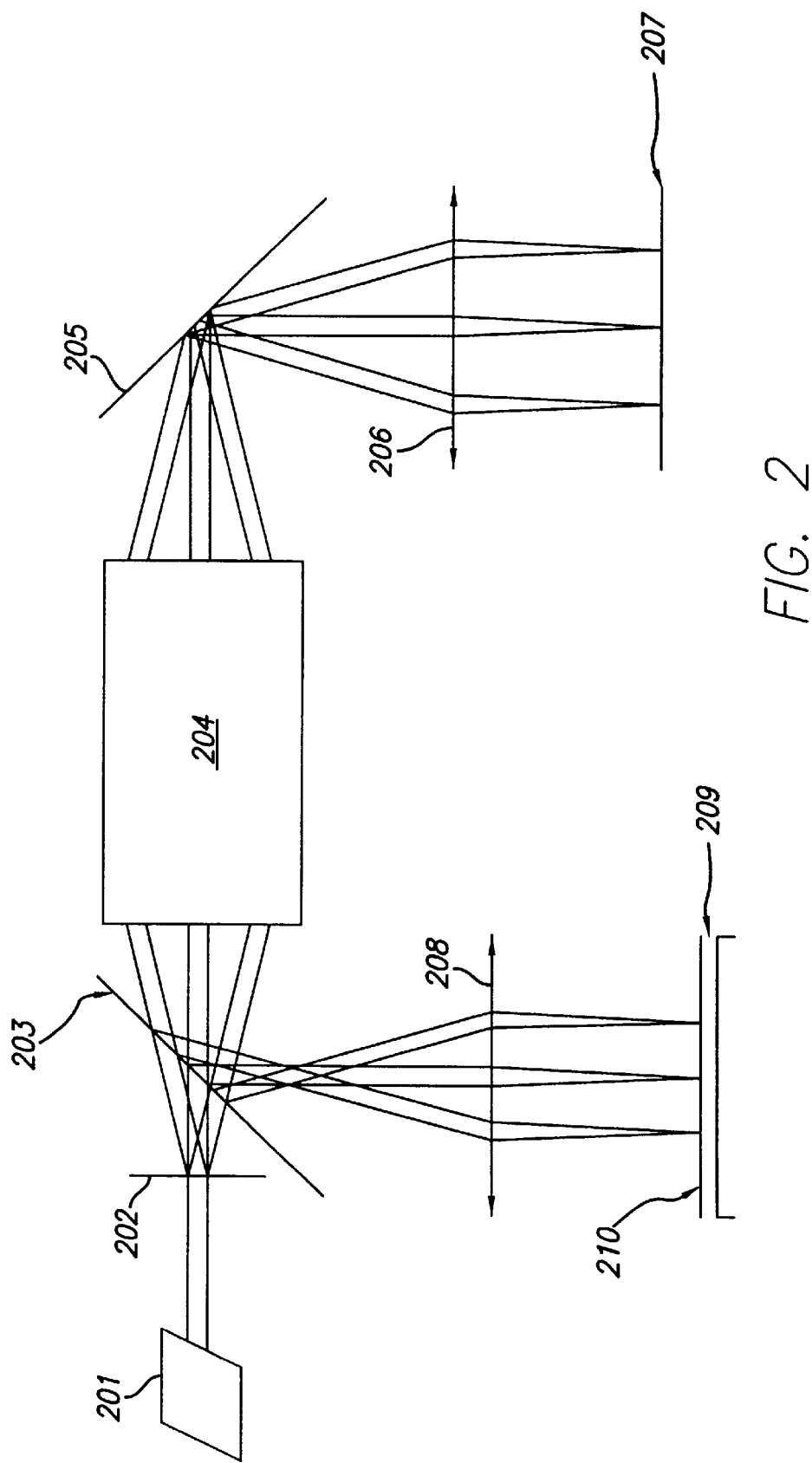
FIG. 2 is an alternate embodiment of the inventive system disclosed herein with sensing occurring at an alternate orientation to the specimen.

An alternative mechanization is illustrated in FIG. 2. As shown therein, laser 201 provides light energy to the one or two dimensional diffraction element 202, which splits the beam into multiple beams. The light energy passes through beamsplitter 203, and thereafter to telescope 204, which collects the multiple beams. Light then passes to mirror or deflector 205, which expands the light energy toward objective 206, collecting the light and providing multiple beams to sample 207. Light passes back through objective 206, reflects from mirror or deflector 205, passes through telescope 204, and deflects from beamsplitter 203 downward, through focusing lens 208, and onto detector array 209. If the detector array 209 comprises an array of relatively large discrete detectors, a pinhole array 210 is placed in front of the detector in a manner described below.

As may be appreciated by those of skill in the art, the number of spots or points in the array may vary while still within the teachings of the invention and providing larger scan areas than previously known. For example, a 10 spot by 10 spot or 100 spot array may be employed, or a one spot by 10 spot, or 10 spot total array may be created using the diffraction elements and mechanizations illustrated in FIGS. 1 and 2.

Figure 3:
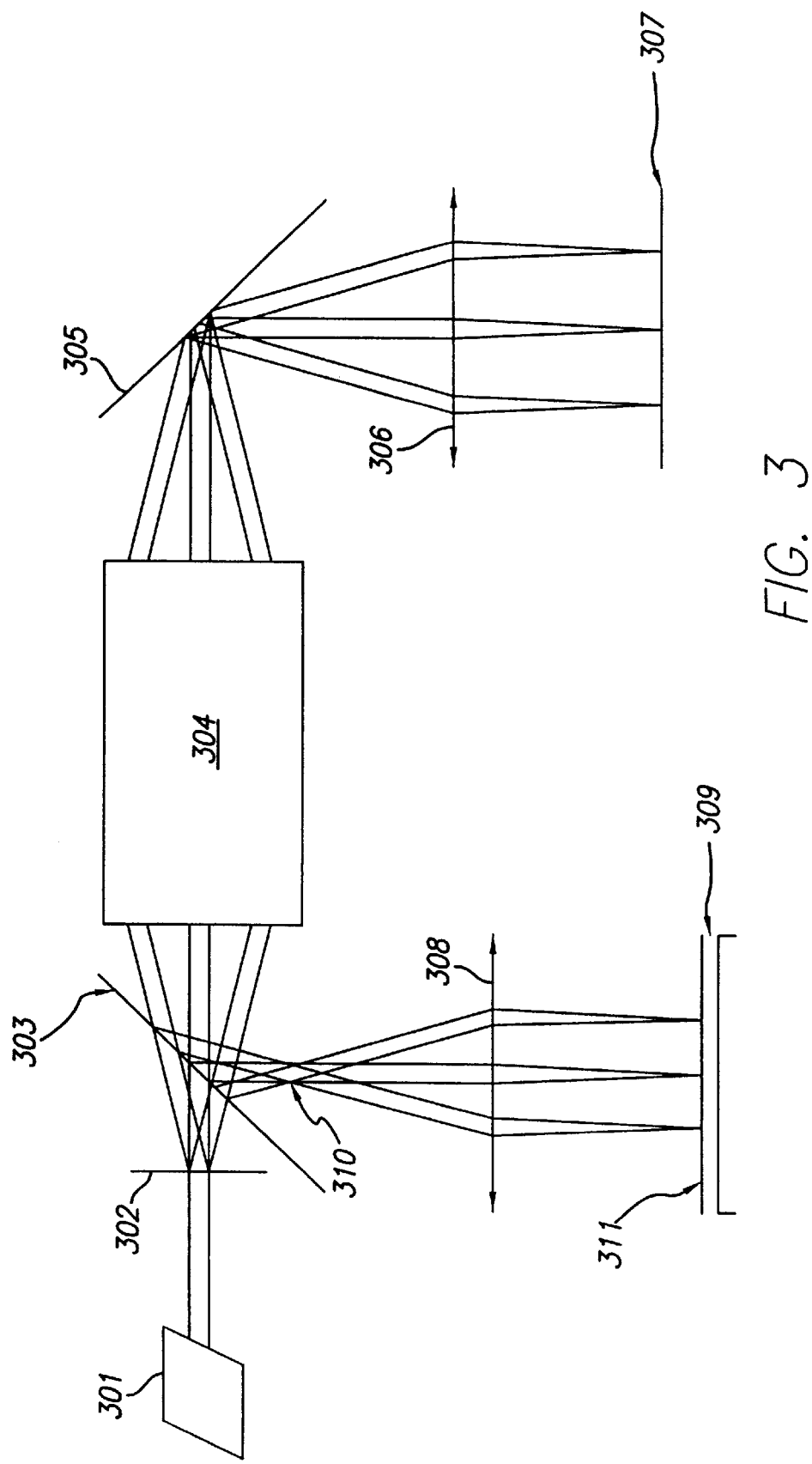
FIG. 3 presents an embodiment of the system which operates in a dark-field imaging/inspection mode.

FIG. 3 presents an embodiment of the system which operates in a dark-field imaging/inspection mode. As shown therein, the system is similar to that shown in FIG. 2, and all the components illustrated in FIG. 3 have the same functionality as their corresponding components in FIG. 2. A stop, or obstruction, may be placed at focal point 310 in the manner described below.

The configuration illustrated in FIG. 3 utilizes the fact that when a beam of light is focused onto a flat surface, the reflected beam will essentially reconstitute its original shape and size after passing through the same focusing system. Thus, if a physical stop is placed along the reflected path in the path of the beam so that the physical extent of the beam essentially matches the size of the stop, no light reaches any element of the detector. This arrangement results in a low (essentially zero) signal. When the part of the sample directly under each beam is in focus and featureless, the signal due to that part of the sample results in a dark background. In a situation where the portion of the sample under a particular beam has some kind of scattering structure, such as an edge, the scattered part of the beam will cover a greater solid angular distribution than the illumination beam. In this case, the obstruction that is placed so as to eliminate a beam equal in size to the illumination beam is not able to eliminate all of the scattered radiation. Therefore, a certain amount of light which falls outside the diameter of the obstruction reaches the detector and produces a signal. Since this signal only forms in the presence of a scattering feature on the interrogated region of the sample, the system acts as a darkfield imaging/inspection modality.

Where a system employs a plurality of beams as opposed to a single beam, all the beams reflected off the sample re-converge upon the same central region before diverging outward again. It is therefore only necessary to place a single obstruction at this position to ensure that all beams are subjected to dark-field detection.

A prerequisite for maximum efficiency of this darkfield arrangement is that the optical train used to illuminate the sample should be capable of carrying higher spatial frequencies than those required to constitute the illumination foci. This condition implies that the numerical aperture of the focusing system must be larger than would normally be required to generate the required spot size of each beam. Upon illumination only the relatively central region of the illumination optics is utilized. However, the scattered radiation from each interrogated part of the sample fills a larger part of the aperture, thus producing a plurality of larger sized beams. The central portion of these beams is obstructed by the stop, as discussed above, and the detected signal for each beam is that due to the scattered radiation, indicating darkfield imaging/inspection. In practice, such an arrangement is easily implemented, especially, but not exclusively, when a two dimensional fanning of the beams is used. Such an approach constitutes a fast inspection methodology, since the size of each beam can be substantially larger than would be the case for high resolution microscopy, allowing for a much shorter inspection time per sample. At the same time, the sensitivity of the technique remains high due to the fact that darkfield inspection is employed.

For the system to perform confocal imaging, each detector must effectively be a pinhole. Confocal imaging is best achieved by placing an array of pinholes directly in front of the detector array such that the center of each pinhole is substantially aligned with the center of each element of detector array. In such an arrangement, the axis of each beam passes through the center of its respective pinhole. As is known to those skilled in the art, the size of the pinhole is determined based on the size of the focal spot size of the sample as well as the magnification that exists between the sample plane and the pinhole plane. The pinholes can be produced using a variety of techniques, such as laser drilling, in an otherwise opaque substrate.

Since the size of each pinhole is significantly larger than the corresponding focal spot, the need for precise alignment, and the requirement for extreme mechanical stability of the pinhole array are avoided. In essence, once the stability of the sample/beams combination is assured (a task required of all high resolution imaging), the stability of the pinhole array itself is not critical. This permits both easy operation and alignment of the array.

In the arrangement illustrated in FIGS. 1, 2, and 3, the light beam passes through a beamsplitter, such as beamsplitter 203. The passage of light introduces some spherical aberration between the adjacent beams in the multibeam arrangement. The result of the aberration of the beams passing through the beamsplitter is that the origin of the splitting of the beams appears to move through the axial direction for different angular locations of the beams. The shifting has two components, a relatively large and common component, which can be compensated for by relocating the affected optics, such as the telescope, and a much smaller position-dependent part, which may be negligible especially for relatively thin beamsplitters. Thus the beamsplitting does not significantly detract from overall performance.

Scanning in the system illustrated in FIGS. 2 and 3 may occur in various ways. The system may pass the sample iteratively by scanning it beneath the objective in a raster fashion in the x and y directions, or alternately by spinning the sample about a central axis. Using these types of scanning methods, the position of the focused spots on the CCD or sensor array elements is fixed. Alternately, the system may employ a mechanical raster scanning arrangement of the beams using a scanning arrangement such as a resonant mirror scanner. In this case, both the sample and the beams are mechanically rastered. In this situation, for example, the beams may repeatedly move backward and forward in the x direction while staying fixed in the y direction, while the sample makes smaller movement in the y direction and does not move in the x direction.

Figure 4:
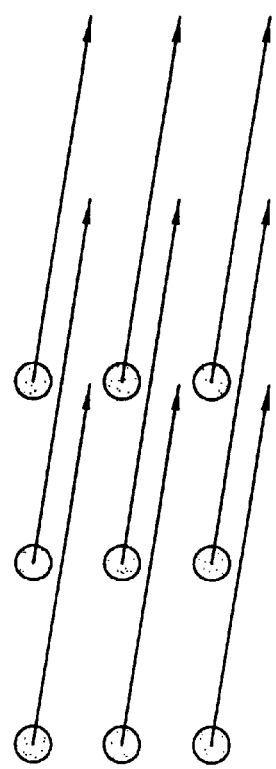
FIG. 4 presents an arrangement of the focal spots and the resulting scan line for each focal spot in accordance with the current invention.

The arrangement of the focal spots and the resulting scan line for each are schematically shown in FIG. 4. The system must ensure that upon the completion of the scan in one direction, proper sampling of data is achieved. Proper data sampling must occur both along the linescan direction and perpendicular thereto. Proper data sampling is achieved along the linescan direction by requiring electronic data sampling as the scan is executed at the required rate. For example, if 3 samples, in each direction, per point spread function (i.e. the optical spot size) are required, then data sampling is generated at a particular detector in the detector array at least 3 times per time period necessary for a sample/beam to traverse each other by a distance equal to the spot size. To ensure proper sampling in the direction perpendicular to the linescan, the system provides for the angle between the columns of the spot array and the fast scan direction to be such that the separation of the scan lines generated by each spot is approximately $\frac{1}{3}$ (for 3×3 sampling) of the spot size. Under these circumstances, the sampling per point spread function of each focal beam is the required 3×3. This procedure applies to other sampling schemes as well, such as an A×B sampling, where the sampling along the fast linescan direction will be A times per transit time of the sample over each focal spot. The separation between adjacent lines in this situation will be 1/B of the spot size.

The reconstruction of the acquired two-dimensional image involves a shifting of the sampled data in time such that the displayed or processed data are properly de-skewed. This is easily achieved using ordinary computing techniques, since the system has precise knowledge of the amount of shifting required per channel.

Figure 5:
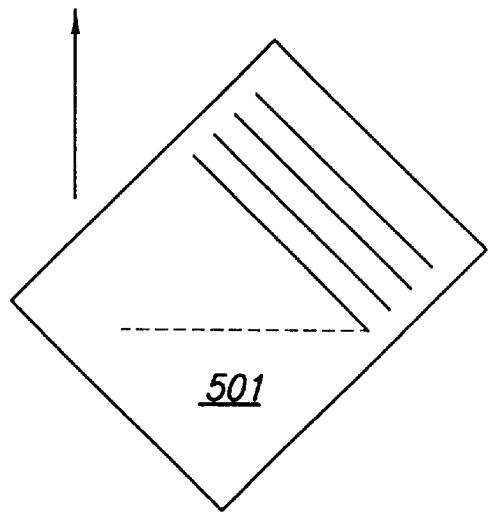
FIG. 5 shows a scanning technique for patterned wafer specimens in accordance with the current invention and the relative orientation of the wafer with respect to the scanning lines, wherein the angles are exaggerated to illustrate the inventive method.

Another potential scanning technique for the current invention may be used during the inspection of a patterned wafer. During inspection of a patterned wafer, a considerable throughput advantage exists for maintaining the Manhattan geometry alignment with the inspection direction. Particular attention must be paid to providing the capability wherein the trace of each scanning beam remains parallel to the "streets" as the scanning beam traverses the wafer. Using dual motion as described above, movement of each must be coordinated to properly observe the Manhattan "streets". To achieve proper orientation and observation, the stage speed in the cross direction is set at the ratio of the distance between the first and last lines generated by the spots divided by the period of the scanner. For example, if the scanner operates at 500 Hz and the separation between the first and last scanner line is 80 microns, the stage speed is set at (80×0.001)×500=40 millimeters/second. The orientation of the wafer with respect to the scanning lines is illustrated in FIG. 5, wherein the wafer 501 is oriented at an angle whose sine is given by:

$$\frac{\text{(fraction of scan time which is active)} \times \text{(stage speed)}}{\text{width of the swath}}$$

Note that the angular orientations of the scan direction relative to the stage direction are exaggerated for clarity. This angular orientation and speed calculation ensures that the pattern covered by the scanning beams cover the Manhattan geometric path.

When the wafer reaches the end of a swath, the scanning must occur in the opposite direction. The same strategy as described above may be employed, with the exception of a reversal of the fast scanning direction, or a re-orientation of the stage or scanner to provide the reverse angular disparity between the scanner and the wafer. This reverse scanning technique may be employed by using a bidirectional scanner such as a galvo mirror and taking data on the reverse path across the wafer. Alternately, the stage may perform a fast return to one swath width from the position where the prior scan began, and the next swath of data is then taken in the same manner as before.

In general, if the laser beam is split in two directions using a diffractive element into an n×m array of individual beams, the reflected light is collected and directed onto n×m separate detectors, wherein each detector results in a separate output. Placement of a pinhole in front of each detector provides a parallel confocal system.

An alternate embodiment of the detector or sensor 313 would be a multiple PMT array, or the reflected beams could be focused with appropriate magnification onto a two dimensional CCD array, as shown in FIGS. 1, 2, and 3. The axis of such a CCD array is aligned with the direction of the scan. When using the CCD array, the confocal effect is still attained since any defocus spreads the energy outside the intended pixels. Since adjacent pixels are not used for detection, the reception of photons by these adjacent pixels is of no consequence.

Timing between the sample data from each detector permits the composition of the image in two dimensions, eliminating the beam stagger effect. Such compensation is a software alterable feature which may be performed in real time, or by post processing of data.

In applications where severe requirements exist for the separation of the top layer and the underlying circuitry, such as in the inspection of CMP wafers, the system employs shorter wavelength lasers, such the 266 nm quadrupled Nd system.

With respect to illumination angle, the system may employ normal or oblique angular illumination, and collection can be performed using normal, near normal, single darkfield, or double darkfield modes. In the case of oblique illumination, the two dimensional distribution of the spots causes a level of defocus among the spots. However, for spot sizes desired for some systems, such as 50 by 20 micron spots for a system similar to the SP1 system manufactured by KLA-Tencor Corporation of San Jose, Calif., the degree of defocus is insignificant. The orientation of the spots on the specimen with respect to the scan direction, i.e. the specimen rotation, is similar to that associated with microscopy. The result is m by n concentric circles due to wafer rotation, and separation between the spots as set by the transmission, filtering, and lensing characteristics of the system satisfy any predetermined sampling requirements.

The scattered radiation is collected by the imaging lens and is re-imaged onto the elements of a high sensitivity two dimensional detector array, such as PMT, APD, or photodiode/preamplifier arrays. For near-normal or single darkfield imaging, the system does not provide a defocusing problem due to the imaging lens. The individual detector size of a multiple photodiode or PMT array can range from a 1×1 millimeter area to a 2.5×2.5 millimeter area. Any defocus at the detector plane due to oblique collection simply spreads the energy over a larger area of the intended detector, but still well within the boundaries of the intended detector, thereby inhibiting crosstalk in the detector arrays. Some crosstalk inevitably results in the detector arrays, but such cross talk for particular arrays is of known quantity and can be compensated for. Also, the type of detector used may decrease the amount of crosstalk, as different detectors have known characteristics which provide less crosstalk problems than other detectors.

With respect to rotary scanning devices, such as the KLA-Tencor SP1, the result of the use of parallel detectors is that the instantaneous area being observed is much larger than previous applications. Thus, a system employing the massively parallel arrangement disclosed herein does not require the fast rotation of the wafer, currently at approximately 4500 rpm for the SP1. For an m×n spot/detector arrangement, the rotation speed on average decreases to 4500/(m×n). Such a speed provides for relatively simple edge handling of the specimen without excessive forces applied thereto.

The current system applies to the scanning of patterned wafers as well. To keep all the points in focus on the wafer, the illumination incidence angle for single darkfield or near normal illumination is kept at or near normal. In near normal illumination, collection optics are fully focused for all points. In single dark field collection, a certain amount of defocus exists among the image points across the field. Since the collection site per element is large, defocus should again not cause excessive crosstalk.

The inspection speed can also be increased from that currently available by incorporating a fast scanner, such as a resonant scanner or polygon, into the design. However, the massive parallelism of the system drastically reduces the required scan speed for the scanner. For example, using a resonant scanner or polygon operating at 1 kHz, together with an array of 10 beams by 10 beams, or 100 beams, provides an equivalent scanning speed of 100 kHz. This provides a faster linescan speed compared with a single AOD or polygon scanner.

While the invention has been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

I claim:

1. A system for inspecting a specimen, comprising:
   a light generating device;
   a diffractive element receiving light energy transmitted by said light generating device and transmitting diffracted light energy;
   an optical arrangement receiving the diffracted light energy transmitted by said diffractive element;
   an objective receiving light energy from said optical arrangement;
   wherein said system produces an apparent plane of splitting of light; and wherein said system further comprises:
      a focusing lens receiving light energy from said objective, said focusing lens having a focal plane, said focusing lens receiving light energy from said objective;
      wherein the focusing lens focal plane substantially coincides with the apparent plane of splitting of light.

2. The system of claim 1, wherein said diffractive element splits light energy received from said light generating device thereby providing multiple light beams, and wherein multiple light beams contact said specimen.

3. The system of claim 1, wherein said diffractive element comprises a diffractive element from the group including a one dimensional grating and a two dimensional grating.

4. The system of claim 1, wherein said detector arrangement comprises a detector from the group comprising a CCD detector, a photodiode array, and a multiple PMT array.

5. The system of claim 1, wherein said diffractive element comprises an optical element from the group including a diffraction grating and a digital optical element.

6. The system of claim 1, wherein inspection comprises linear scanning.

7. The system of claim 1, further comprising a detector arrangement receiving light energy from said focusing lens.

8. The system of claim 1, wherein the optical arrangement comprises at least one from a group comprising:
   a beamsplitter; and
   a telescoping lens group.

9. The system of claim 1, wherein the optical arrangement comprises a telescope having at least one lens.

10. The system of claim 1, wherein the optical arrangement comprises a telescopic lensing arrangement.

11. The system of claim 1, wherein the optical arrangement comprises a lensing arrangement.

* * * * *